United States Patent
Hayakawa et al.

(10) Patent No.: US 9,611,379 B2
(45) Date of Patent: Apr. 4, 2017

(54) PREPARATION OF CELLULOSE ETHER POWDER

(71) Applicant: SHIN-ETSU CHEMICAL CO., LTD., Tokyo (JP)

(72) Inventors: Kazuhisa Hayakawa, Joetsu (JP); Shingo Niinobe, Joetsu (JP); Hironao Saito, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 107 days.

(21) Appl. No.: 14/053,700

(22) Filed: Oct. 15, 2013

(65) Prior Publication Data

US 2014/0109798 A1 Apr. 24, 2014

(30) Foreign Application Priority Data

Oct. 18, 2012 (JP) .................. 2012-230727

(51) Int. Cl.

| | |
|---|---|
| *C08L 1/26* | (2006.01) |
| *C08L 1/28* | (2006.01) |
| *C08J 3/12* | (2006.01) |
| *C09D 101/26* | (2006.01) |
| *A61K 8/73* | (2006.01) |
| *A61Q 19/00* | (2006.01) |
| *A61K 8/02* | (2006.01) |
| *A23L 29/262* | (2016.01) |

(52) U.S. Cl.
CPC ............... *C08L 1/28* (2013.01); *A23L 29/262* (2016.08); *A61K 8/022* (2013.01); *A61K 8/731* (2013.01); *A61Q 19/00* (2013.01); *C08J 3/12* (2013.01); *C08J 3/128* (2013.01); *C08L 1/26* (2013.01); *C08L 1/284* (2013.01); *C09D 101/26* (2013.01); *A61K 2800/10* (2013.01); *A61K 2800/41* (2013.01); *A61K 2800/412* (2013.01); *C08J 2301/26* (2013.01); *C08L 2205/18* (2013.01)

(58) Field of Classification Search
CPC ....... A23L 29/262; A61K 8/022; A61K 8/731; C08L 1/26; C08L 1/28
USPC ...................................................... 106/501.1
See application file for complete search history.

(56) References Cited

FOREIGN PATENT DOCUMENTS

| | | | | |
|---|---|---|---|---|
| JP | 04346919 A | * 12/1992 | ............... | A61K 9/22 |
| JP | 08-154643 A | 6/1996 | | |
| JP | 11-322801 A | 11/1999 | | |
| JP | 2002370963 A | * 12/2002 | ............... | A61K 7/48 |

* cited by examiner

*Primary Examiner* — Kaj K Olsen
*Assistant Examiner* — Alexander Polyansky
(74) *Attorney, Agent, or Firm* — Westerman, Hattori, Daniels & Adrian, LLP

(57) ABSTRACT

Cellulose ether powder is prepared in a safe and easy way by first adding a surfactant solution to surfaces of water-soluble cellulose ether particles, and then adding a tannin solution thereto. The powder thus prepared is free of bitterness and readily dissolvable in cold water without forming clumps.

6 Claims, 1 Drawing Sheet

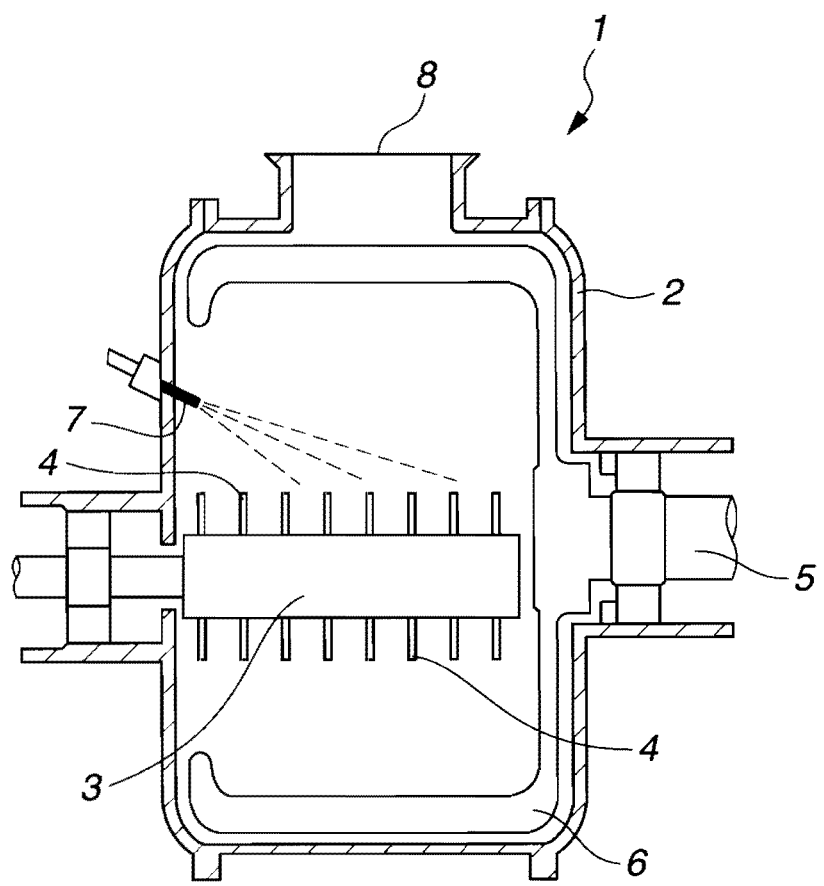

PREPARATION OF CELLULOSE ETHER POWDER

CROSS-REFERENCE TO RELATED APPLICATION

This non-provisional application claims priority under 35 U.S.C. §119(a) on Patent Application No. 2012-230727 filed in Japan on Oct. 18, 2012, the entire contents of which are hereby incorporated by reference.

TECHNICAL FIELD

This invention relates to a method for preparing a cellulose ether particle powder which is added to foods (inclusive of beverages), drugs, cosmetics (e.g., shampoo and rinse), and coating compositions as a sizing agent, thickener, binder or the like.

BACKGROUND ART

Beverage, shampoo, rinse, paint and the like must be given some viscosity in order to facilitate dispensing from containers or spreading on use. To this end, water-soluble cellulose ethers such as alkyl celluloses and hydroxyalkyl alkyl celluloses are often added as the thickener. Also an aqueous solution of cellulose ether must be prepared to form a surface coating for facilitating granulation or hiding the bitterness of pharmaceutical or other preparations, or imparting thickness to food or beverage.

If cellulose ether in powder form is directly admitted into cold water, particle surfaces are immediately dissolved to become viscous, and particles attract each other and agglomerate together, forming agglomerates having a size from rice grains to adzuki beans, known as "clumps" or "lumps". The surface of "clumps" is a coating having a high viscosity, which becomes a barrier against further penetration of water. It will take at least one day until complete dissolution.

Patent Document 1 discloses to add or spray 2 to 20 parts by weight of a glycol and/or nonionic surfactant having a HLB of 3 to 17 to 100 parts by weight of cellulose ether.

In Patent Document 1, however, when it is desired to prepare an aqueous solution having a concentration of at least 2% by weight, clumps or lumps are likely to form. This problem may be overcome by treatment with a large amount of surfactant solution, but another problem arises. Since surfaces of cellulose ether particles become readily dissolvable, these particles agglomerate together to form large agglomerates. The dissolution rate in cold water is significantly retarded.

Patent Document 2 discloses a cold pack for food which is prepared by attaching a safe food additive, tannin to cellulose ether so as to be water-insoluble, and adding another food additive such as sodium hydrogencarbonate or sodium carbonate thereto so that the cellulose ether is water-soluble.

In Patent Document 2, more tannin must be attached for further improvement in dissolution. The more amount of tannin can add to bitterness when a significant amount of cellulose ether is used as a sizing agent, thickener or binder.

CITATION LIST

Patent Document 1: JP-A H11-322801
Patent Document 2: JP-A H08-154643

SUMMARY OF INVENTION

An object of the invention is to provide a method for preparing a cellulose ether particle powder in a safe and easy way, which powder is free of bitterness and readily dissolvable in cold water.

The inventors have found that a cellulose ether particle powder can be prepared by first adding a surfactant solution to water-soluble cellulose ether particles, and later adding a tannin solution thereto. This method ensures safe and easy preparation, and the cellulose ether powder thus obtained is free of bitterness and readily dissolvable in cold water.

The invention provides a method for preparing a cellulose ether particle powder, comprising the steps of adding a surfactant solution to surfaces of water-soluble cellulose ether particles, and then adding a tannin solution thereto.

Typically, the surfactant has a HLB in the range of 14 to 19. It is preferably selected from among fatty acid glycerol esters, sucrose fatty acid esters, polyoxyethylene fatty acid esters, sorbitan glycol esters, sorbitan fatty acid esters, carboxylic acid derivative salts, and sulfonic acid derivative salts.

Also typically, the tannin is a hydrolyzable tannin. Preferably, 0.2 to 0.9 part by weight of the tannin is added per 100 parts by weight of the water-soluble cellulose ether.

Advantageous Effects of Invention

By the method of the invention, a cellulose ether particle powder can be prepared in a safe and easy way. The powder thus prepared is free of bitterness and readily dissolvable in cold water without forming "clumps" or "lumps."

BRIEF DESCRIPTION OF DRAWING

FIG. 1 is a schematic cross-sectional view of one exemplary agitation mixer used in the practice of the invention.

DESCRIPTION OF PREFERRED EMBODIMENTS

According to the method of the invention, a cellulose ether particle powder is prepared by adding a surfactant solution to surfaces of water-soluble cellulose ether particles, and later adding a tannin solution thereto.

The water-soluble cellulose ether used herein is not particularly limited. Any cellulose ethers which are obtained by etherifying celluloses so as to be water soluble are useful. Suitable cellulose ethers include alkyl celluloses, hydroxyalkyl celluloses, hydroxyalkyl alkyl celluloses, and hydroxyalkyl alkyl cellulose stearoxy ethers. Among others, preference is given to methyl cellulose (MC), hydroxypropyl methyl cellulose (HPMC), hydroxyethyl methyl cellulose (NEMC), hydroxyethyl ethyl cellulose (HEEC), hydroxypropyl cellulose (HPC), and hydroxyethyl cellulose (HEC).

Illustrative examples include alkyl celluloses such as water-soluble methyl cellulose (MC) having a methoxyl content of 10 to 40 wt %; hydroxyalkyl celluloses such as hydroxypropyl cellulose (HPC) having a hydroxypropoxyl content of 40 to 70 wt % and hydroxyethyl cellulose (HEC) having a hydroxyethoxyl content of 30 to 70 wt %; hydroxyalkyl alkyl celluloses such as hydroxypropyl methyl cellulose (HPMC) or hydroxyethyl methyl cellulose (HEMC) having a methoxyl content of 10 to 40 wt % and a hydroxylalkyl content of 3 to 30 wt % effective for improving solubility and hydroxyethyl ethyl cellulose (HEEC) having an ethoxyl content of 5 to 20 wt % and a hydroxyethoxyl content of 10 to 45 wt %; and hydroxyalkyl alkyl cellulose stearoxy ethers having a stearyloxyhydroxypropoxyl content of 0.2 to 0.6 wt %.

Preferably, the water-soluble cellulose ether has a weight average molecular weight (Mw) of 1,000 to 2,000,000, more preferably 10,000 to 1,500,000, and even more preferably 20,000 to 1,000,000. If Mw is less than 1,000, the cellulose ether may be fully soluble and intrinsically free of the "clump" problem. If Mw exceeds 2,000,000, the cellulose ether may be too viscous and prone to form "clumps." It is noted that Mw is measured by a gel permeation chromatography/light scattering (GPC/LS) coupled system.

Preferably, the water-soluble cellulose ether has an average particle size of 50 to 400 μm, more preferably 60 to 250 μm, and even more preferably 60 to 200 μm. If the average particle size is less than 50 μm, the cellulose ether powder obtained from the method may form "clumps" when admitted into cold water. If the average particle size exceeds 400 μm, a long time may be taken until the cellulose ether powder is dissolved. It is noted that the average particle size of water-soluble cellulose ether is measured by applying water-soluble cellulose ether powder to a stack of sieves having different opening sizes as prescribed by JIS Z8801-1982 "Test Sieves", and plotting the cumulative percent of the residue on each sieve and the opening size of that sieve on a Rosin-Rammler chart, with the particle size at which the cumulative percent reaches 50% being assumed as the average particle size.

The water-soluble cellulose ether used herein may be either one having a low water content of less than 5 wt % as a result of drying and grinding steps or one having a certain water content without any treatment. The latter water-soluble cellulose ether may have a water content of preferably 5 to 90 wt %, more preferably 10 to 70 wt %. If the water content exceeds 90 wt %, water-soluble cellulose ether particles may quickly agglomerate into larger particles upon fluidization.

The surfactant used herein is preferably nonionic and specifically has a hydrophilic-lipophilic balance (HLB) of preferably 14 to 19, more preferably from more than 15 to 17. If HLB is less than 14, the effect of suppressing "clump" formation when the cellulose ether particle powder is admitted into cold water may be weakened. It may be difficult to avoid "clump" formation, particularly when an aqueous solution having a concentration of at least 2 wt % is prepared using the cellulose ether particle powder. The reason is that a surfactant having an HLB which is less than the HLB (=11) of water-soluble cellulose ether and thus on the lipophilic side exerts poor wettability and has a detrimental effect on dissolution in cold water, whereas a surfactant having an HLB in the range of 14 to 19 exerts good wettability and has no detrimental effect on dissolution in cold water.

Examples of suitable surfactants include fatty acid glycerol esters such as decaglycerol monolaurate and decaglycerol monomyristate; sucrose fatty acid esters such as sucrose laurate; polyoxyethylene fatty acid esters such as polyoxyethylene stearate; sorbitan glycol esters such as polyethylene glycol sorbitan ester; sorbitan fatty acid esters such as sorbitan monooleate; carboxylic acid derivative salts such as sodium oleate, sodium stearate and sodium laurate; and sulfonic acid derivative salts such as sodium tetradiphenylstyrenesulfonate and sodium di(2-ethylhexyl)sulfosuccinate. Inter alia, preferred are decaglycerol monolaurate, decaglycerol monomyristate, sucrose fatty acid esters, polyoxyethylene fatty acid esters, polyethylene glycol sorbitan ester, carboxylic acid derivative salts, and sulfonic acid derivative salts.

Preferably the surfactant is added in an amount of 0.4 to 3.0 parts, more preferably 0.6 to 2.0 parts by weight per 100 parts by weight of the water-soluble cellulose ether. If the amount of the surfactant added is less than 0.4 part, the effect of suppressing "clump" formation when the cellulose ether particle powder is admitted into cold water may be weakened. It may be difficult to completely avoid "clump" formation, particularly when an aqueous solution having a concentration of at least 2 wt % is prepared using the cellulose ether particle powder. If the amount of the surfactant added exceeds 3.0 parts, surfaces of water-soluble cellulose ether particles may be dissolved so that they agglomerate into larger particles, retarding dissolution when admitted into cold water.

Examples of tannin used herein include hydrolyzable tannins in which aromatic compounds such as gallic acid and ellagic acid are in ester bond with sugar such as glucose and which are hydrolyzable with acids, alkalis or enzymes into polyfunctional phenolic acid and polyhydric alcohol (e.g., sugar); and condensable tannins having a flavanol structure-bearing compound polymerized therewith. Inter alia, hydrolyzable tannin is preferred in that dissolution in cold water is achievable in a less amount.

Preferably tannin is added in an amount of 0.2 to 0.9 parts, more preferably 0.3 to 0.7 parts by weight per 100 parts by weight of the water-soluble cellulose ether. If the amount of tannin added is less than 0.2 part, the effect of suppressing "clump" formation when the cellulose ether powder is admitted into cold water may be weakened. It may be difficult to completely avoid "clump" formation, particularly when an aqueous solution having a concentration of at least 4 wt % is prepared using the cellulose ether powder. If the amount of tannin added exceeds 0.9 part, tannin's bitterness may become perceivable upon dissolution in cold water, prohibiting addition to food and beverage, and the product cost may be increased. It may be difficult to completely avoid development of tannin's bitterness, particularly when an aqueous solution having a concentration of at least 4 wt % is prepared using the cellulose ether powder.

The method for preparing a cellulose ether particle powder according to the invention starts with the step of adding a surfactant solution to water-soluble cellulose ether. When the surfactant solution is added, the surfactant solution may be used as such or after dissolution in water. When a surfactant aqueous solution is used, it is preferred from the standpoint of uniform addition that the solution have a concentration of 1 to 50 wt %, more preferably 1 to 30 wt % of the surfactant.

A mixer is used when the surfactant solution is added. Suitable mixers include spray mixers, typically Spartan Granulator (Dalton Co., Ltd.), fluidized bed mixers, Flexomix (Hosokawa Micron Corp.), ploughshare type mixers (Lodige GmbH and Pacific Machinery & Engineering Co., Ltd.), Nauta mixers such as Hi-Blender, cone type blenders, and V blenders. Inter alia, a spray mixer is preferred since it ensures that a surfactant solution is uniformly added to a uniform dispersion of water-soluble cellulose ether particles.

Preferably, the surfactant solution is fed at a rate of 1 to 500 g/min, more preferably 2 to 20 g/min. Too low a feed rate may adversely affect productivity since a long time is necessary until the desired product is obtained. At too high a feed rate, the surfactant solution may not come in uniform contact with the cellulose ether.

FIG. 1 illustrates one exemplary agitation mixer which is advantageously used in the practice of the invention and commercially available under the trade name of Spartan Granulator from Dalton Co., Ltd. The mixer generally designated at 1 includes a tank 2. A first rotating shaft (or rotor) 3 is rotatably mounted in the tank 2 and horizontally extended inward from a portion of one side wall of the tank 2 which is disposed near the center in height direction. The rotor 3 is provided with a plurality of impeller pins 4 projecting radially from its outer periphery. The rotor 3 is rotated in one direction by a drive (not shown) such as a motor while the impeller pins 4 are integrally rotated in the same direction. A second rotating shaft 5 is rotatably mounted in the tank 2 at another side wall and opposed to the rotor 3. The second rotating shaft 5 is rotated in a direction opposite to the rotor 3 (i.e., counter-rotated) by a drive (not shown) such as a motor. The second rotating shaft 5 is provided with ribbon or cage-shaped mixing arms 6 which each extend radially along the inside of the other side wall and axially along the top and bottom walls of the tank 2. As the second rotating shaft 5 is counter-rotated, the arms 6 are integrally rotated in the opposite direction. A two-fluid nozzle 7 is provided in one sidewall of the tank for feeding compressed air and the surfactant solution or tannin solution into the tank. The tank 2 includes an inlet 8 at the top for feeding the water-soluble cellulose ether.

The water-soluble cellulose ether particles are fluidized at a suitable rate. An agitation mixer is like Spartan Granulator as shown in FIG. 1, in which a rotor with a plurality of impeller pins is horizontally mounted at the center of the tank. Provided that the mixer tank has a diameter of 250 mm and a volume of 2 liters and is charged with 0.5 kg of water-soluble cellulose ether particles and/or water-soluble hydroxyalkyl alkyl cellulose polymer particles, the rotor with impeller pins is preferably rotated at 1,500 to 10,000 rpm, more preferably 2,000 to 7,000 rpm. If the rotational speed is too low, the surfactant solution may not come in uniform contact with the cellulose ether. If the rotational speed is too high, the impeller pins may be severely worn and the mixer be damaged.

It is desirable to use an agitation mixer having a first horizontal shaft with radial impeller pins and a second horizontal shaft with ribbon or cage-shaped mixing arms which enclose the impeller pins and rotate around the impeller pins in a counter direction, as illustrated in FIG. 1. While powder particles are agitated and fluidized by the impeller pins rotating at a high speed, the arms create countercurrent flows. Then the overall fluid is uniformly agitated in the tank without stagnation. For this reason, the provision of a second shaft with ribbon or cage-shaped arms which turn around the impeller pins in a counter direction is desirable. The second shaft with arms is preferably counter-rotated at 10 to 1,000 rpm, more preferably 20 to 100 rpm. If the rotational speed is too low, some portions of powder may stagnate. If the rotational speed is too high, particles impinge against each other too fast, allowing for pulverizing action.

Typically a two-fluid nozzle depicted at 7 in FIG. 1 is used as the means for adding the surfactant solution to the water-soluble cellulose ether. As to the structure of a two-fluid nozzle, the nozzle includes a central nozzle for injecting the surfactant solution and an outer nozzle enclosing the central nozzle for injecting compressed air. Then the surfactant solution is carried by compressed air and injected to surfaces of water-soluble cellulose ether particles. The two-fluid nozzle preferably has an injection angle of 30° to 110°, more preferably 45° to 100°, and even more preferably 50° to 80°. If the angle of the two-fluid nozzle is outside the range of 30° to 110°, the surfactant solution may attach to the inner wall, impeller pins and/or arms of the mixer rather than cellulose ether particles. The surfactant solution is preferably fed at a rate of 5 to 30 g/min, more preferably 10 to 20 g/min.

When the surfactant solution is fed to the water-soluble cellulose ether particles, the temperature is preferably at 5 to 50° C. At temperature below 5° C., the surfactant solution may become too viscous and may not uniformly attach to the cellulose ether particles. At temperatures above 50° C., aqueous solution including the surfactant solution may evaporate, preventing uniform attachment of the surfactant.

When the surfactant solution is sprayed as droplets and added to the water-soluble cellulose ether particles, the average diameter of droplets is preferably smaller than the average particle size of the water-soluble cellulose ether. Specifically the average diameter of sprayed droplets is up to 1/10, preferably up to 1/50 of the average particle size of water-soluble cellulose ether. If the average diameter of droplets is too large, it may be difficult to achieve uniform addition to all cellulose ether particles in fluidized state. It is noted that the average diameter of droplets is measured by a particle size measurement system based on laser diffractometry.

Next, a tannin solution is added to the surfaces of water-soluble cellulose ether particles having the surfactant solution attached thereto. A solution of tannin in water or an organic solvent such as methanol, ethanol or acetone may be used. It is preferred for uniform addition that the tannin solution have a concentration of 0.5 to 30 wt %, more preferably 2 to 20 wt % of tannin.

Any desired method may be used for adding the tannin solution as long as the tannin solution is uniformly added to the surfaces of water-soluble cellulose ether particles having the surfactant solution attached thereto. The means for adding the tannin solution may be the same as illustrated as the means for adding the surfactant solution. Inter alia, a spray mixer is preferred since it ensures that a tannin solution is uniformly added to a uniform dispersion of the water-soluble cellulose ether particles having the surfactant solution attached thereto. The spray mixer is preferably the same as the spray mixer used for adding the surfactant solution. The feed rate, feed temperature, and average sprayed droplet diameter of the tannin solution may be the same as those of the surfactant solution.

It is essential in the practice of the invention that the addition of a surfactant solution to water-soluble cellulose ether precede the addition of a tannin solution. The reason is that the surfactant solution has so low an interfacial tension that it may penetrate in, spread on, and attach to surfaces of water-soluble cellulose ether particles as a coating of solution, whereas the tannin solution has so high an interfacial tension that it may not penetrate in or spread on surfaces of water-soluble cellulose ether particles. That is, when a surfactant solution is previously added to surfaces of water-soluble cellulose ether particles and a tannin solution is post-added thereto, the interfacial tension between the surfactant solution (already spread on surfaces of water-soluble cellulose ether particles) and the tannin solution is low, allowing the tannin solution to uniformly spread. Thus a weak bond is uniformly created between a functional group on the surfactant and a functional group on tannin, that is, the surfactant and tannin form a thin water-resistant cross-linked film. When this is admitted into cold water, the crosslinked film serves to retard the penetration rate of water into surfaces of water-soluble cellulose ether particles, preventing formation of "clumps" due to mutual attraction of particles resulting from dissolution of surfaces of water-soluble cellulose ether particles. Inversely, if a tannin solution is previously attached to water-soluble cellulose ether and a surfactant solution is post-added, tannin locally forms a relatively robust crosslinked structure with water-soluble cellulose ether and/or water-soluble hydroxyalkyl alkyl cellulose because tannin has no interfacial tension-reducing ability. When a surfactant solution is added thereafter, the interfacial tension-reducing ability of surfactant allows the surfactant solution to spread on the robust crosslinked portion formed by tannin and water-soluble cellulose ether and a non-crosslinked portion. When this is admitted into cold water, the penetration rate of water into the non-crosslinked portion cannot be retarded, and "clumps" form due to fast dissolution of surfaces of water-soluble cellulose ether particles.

Preferably the water-soluble cellulose ether particle powder as treated with the tannin solution is then dried at a temperature of 60 to 150° C., especially 80 to 120° C. for 0.1 to 24 hours, especially 0.2 to 6 hours. When an aqueous solution is subsequently prepared from such dry cellulose ether powder, the solution may develop a viscosity even in a concentration of 1 to 2 wt %. In addition, the dry cellulose ether powder is free of degradation by mildew attack during shelf storage, and maintains stability as the product. If necessary, the powder may be pulverized after drying. For pulverizing purpose, a knife mill, roller mill or ball mill may be used, for example.

The cellulose ether powder thus obtained preferably has an average particle size of 50 to 8,000 μm, more preferably 60 to 5,000 μm, and even more preferably 70 to 500 μm. If the average particle size of the final powder is less than 50 μm, clumps may form when the powder is admitted into cold water. If the average particle size exceeds 8,000 μm, a long time may be needed until dissolution. The average particle size may be measured in the same manner as that of the starting water-soluble cellulose ether.

EXAMPLE

Examples and Comparative Examples are given below by way of illustration and not by way of limitation.

Examples 1 to 6

There was provided an agitation mixer including a mixing tank, a horizontal rotor disposed at the tank center and having impeller pins, and a horizontal counter-rotating shaft opposed to the rotor and having ribbon-shaped mixing arms which surround the pins and rotate around the pins. It is commercially available under the trade name of Spartan Granulator RMO-4H (working volume 2 L) from Dalton Co., Ltd. To the mixer, 0.5 kg of water-soluble cellulose ether as shown in Table 1 was fed. The rotor with impeller pins was rotated at 4,700 rpm, and the ribbon-shaped mixing arms were counter-rotated around the rotor pins at 25 rpm, thereby keeping water-soluble cellulose ether particles in the fluidized state.

Next, a surfactant solution and a tannin solution were prepared as shown in Table 1 and stored in containers. Through a two-fluid nozzle, the surfactant solution was first sprayed and the tannin solution was then sprayed into the tank, both along with compressed air and at a pressure of 0.03 MPa and a feed rate of 15 g/min. In this way, the solutions were sprayed onto surfaces of water-soluble cellulose ether particles in the amounts shown in Table 1.

There was obtained a cellulose ether powder as spray treated (wet product). By drying the wet product at 105° C. for 4 hours, a cellulose ether powder was completed (dry product).

The average particle size of the cellulose ether powder (wet or dry product) was measured by applying the powder to a stack of sieves having different opening sizes as prescribed by JIS Z8801-1982 "Test Sieves," and plotting the cumulative percent of a fraction remaining on each sieve and the opening size of that sieve on the Rosin-Rammler chart, with the particle size at which the cumulative percent reaches 50% being assumed as the average particle size. The results are shown in Table 1.

The cellulose ether powder (wet or dry product) was admitted to water at 5° C. in such an amount as to form a 2 wt % aqueous solution and agitated at 700 rpm for 7 minutes. The resulting aqueous solution was observed whether or not "clumps" were formed. Only the aqueous solution samples which were free of "clumps" were further examined for viscosity by a Brookfield viscometer and bitterness. The results are shown in Table 1.

Comparative Examples 1 to 8

In Comparative Examples 1 to 6, treatment was carried out as in Examples except that the tannin solution was first sprayed and the surfactant solution was later sprayed. In Comparative Examples 7 and 8, treatment was carried out as in Examples except that either one of the tannin solution and the surfactant solution was sprayed. The formulation and test results are shown in Table 2.

[Water-Soluble Cellulose Ether]
Hydroxypropyl Methyl Cellulose (HPMC)
methoxy substitution degree: 25 wt %
hydroxypropyl substitution degree: 7 wt %
average particle size: 70 μm
weight average molecular weight: 640,000
Methyl Cellulose (MC)
methoxy substitution degree: 30 wt %
average particle size: 120 μm
weight average molecular weight: 910,000
Hydroxyethyl Methyl Cellulose (HEMC)
methoxy substitution degree: 24 wt %
hydroxyethyl substitution degree: 9 wt %
average particle size: 65 μm
weight average molecular weight: 240,000
Hydroxyethyl Ethyl Cellulose (HEEL)
ethoxy substitution degree: 43 wt %
hydroxyethyl substitution degree: 15 wt %
average particle size: 50 μm
weight average molecular weight: 20,000
Hydroxyethyl Cellulose (HEC)
hydroxyethyl substitution degree: 54 wt %
average particle size: 90 μm
weight average molecular weight: 100,000
All these celluloses are available from Shin-Etsu Chemical Co., Ltd.
[Tests]
Formation of "Clumps"

The cellulose ether powder was admitted into water at 5° C. and agitated to form a 2 wt % aqueous solution. The solution was rated Found when "clumps" formed and acceptable (No) when no "clumps" formed.

Taste of Bitterness

The cellulose ether powder was admitted into water at 5° C. and agitated to form a 1 wt % (wet product) or 2 wt % (dry product) aqueous solution. In a test, a person swallowed a 5-ml portion of the solution in the mouth, and judged it as Reject when tasted bitter and acceptable (No) when not bitter.

Although some preferred embodiments have been described, many modifications and variations may be made thereto in light of the above teachings. It is therefore to be understood that the invention may be practiced otherwise than as specifically described without departing from the scope of the appended claims.

TABLE 1

| | Formulation (pbw) | Example 1 | Example 2 | Example 3 | Example 4 | Example 5 | Example 6 |
|---|---|---|---|---|---|---|---|
| Water-soluble cellulose ether | HPMC | 100 | | | 100 | | |
| | MC | | 100 | | | | |
| | HEMC | | | | | 100 | |
| | HEEC | | | | | | 100 |
| | HEC | | | 100 | | | |
| Surfactant | Decaglycerol monolaurate (HLB 15.5) | 1.6 | 0.4 | 0.2 | | | |
| | Decaglycerol monomyristate (HLB 14.5) | | | | | 1.6 | 1.6 |
| | Polyoxyethylene (100) stearate (HLB 18.8) | | | | 3.0 | | |
| | Water | 14 | 10 | 6 | 12 | 14 | 14 |
| Tannin | Hydrolyzable tannin | 0.6 | 0.2 | 0.9 | 0.2 | 0.6 | 0.6 |
| | Water | 4 | 22 | 33 | 33 | 4 | 4 |
| Tests | | | | | | | |
| Wet product | Viscosity (mPa·s) | 100,000 | 1,500 | 18,000 | 90,000 | 110,000 | 40,000 |
| | Average particle size of powder (μm) | 80 | 150 | 250 | 240 | 78 | 70 |
| | Clumps | No | No | No | No | No | No |
| | Bitterness | No | No | No | No | No | No |
| Dry product | Viscosity (mPa·s) | 120,000 | 2,000 | 20,000 | 110,000 | 120,000 | 50,000 |
| | Average particle size of powder (μm) | 75 | 140 | 220 | 210 | 70 | 68 |
| | Clumps | No | No | No | No | No | No |
| | Bitterness | No | No | No | No | No | No |

TABLE 2

| | Formulation (pbw) | Comparative Example 2 | 3 | 4 | 5 | 6 | 7 | 8 |
|---|---|---|---|---|---|---|---|---|
| Water-soluble cellulose ether | HPMC | 100 | | | 100 | | 100 | 100 |
| | MC | | 100 | | | | | |
| | HEMC | | | | | 100 | | |
| | HEEC | | | | | | 100 | |
| | HEC | | | 100 | | | | |
| Surfactant | Decaglycerol monolaurate (HLB 15.5) | 1.6 | 0.4 | 0.2 | | | 1.6 | |
| | Decaglycerol monomyristate (HLB 14.5) | | | | | 1.6 | 1.6 | |
| | Polyoxyethylene (100) stearate (HLB 18.8) | | | | 3.0 | | | |
| | Water | 14 | 10 | 6 | 12 | 14 | 14 | 14 |
| Tannin | Hydrolyzable tannin | 0.6 | 0.2 | 0.9 | 0.2 | 0.6 | 0.6 | 0.6 |
| | Water | 4 | 22 | 33 | 33 | 4 | 4 | 4 |
| Tests | | | | | | | | |
| Wet product | Viscosity (mPa·s) | — | — | — | — | — | — | — |
| | Average particle size of powder (μm) | 80 | 150 | 250 | 240 | 78 | 70 | 80 | 80 |
| | Clumps | Found | Found | Found | Found | Found | Found | Found | Found |
| | Bitterness | — | — | — | — | — | — | — |
| Dry product | Viscosity (mPa·s) | — | — | — | — | — | — | — |
| | Average particle size of powder (μm) | 75 | 140 | 220 | 210 | 70 | 69 | 75 | 75 |
| | Clumps | Found | Found | Found | Found | Found | Found | Found | Found |
| | Bitterness | — | — | — | — | — | — | — |

Japanese Patent Application No. 2012-230727 is incorporated herein by reference.

The invention claimed is:

1. A method for preparing a cellulose ether particle powder, comprising the steps of adding a surfactant solution, wherein the surfactant attaches to surfaces of water-soluble cellulose ether particles, and then adding a tannin solution, wherein the tannin attaches to the surfaces of the water-soluble cellulose ether particles having the surfactant attached thereto.

2. The method of claim 1 wherein the surfactant has a HLB in the range of 14 to 19.

3. The method of claim 1 wherein the surfactant is selected from the group consisting of fatty acid glycerol esters, sucrose fatty acid esters, polyoxyethylene fatty acid esters, sorbitan glycol esters, sorbitan fatty acid esters, carboxylic acid derivative salts, and sulfonic acid derivative salts.

4. The method of claim 1 wherein the tannin is a hydrolyzable tannin.

5. The method of claim 1 wherein 0.2 to 0.9 part by weight of the tannin is added per 100 parts by weight of the water-soluble cellulose ether.

6. The method of claim 1 wherein 0.2 to 0.7 part by weight of the tannin is added per 100 parts by weight of the water-soluble cellulose ether.

* * * * *